United States Patent [19]

Chester et al.

[11] 4,413,056
[45] Nov. 1, 1983

[54] PROCESS FOR THE PREPARATION OF PENICILLINS AND PENICILLIN DERIVATIVES

[75] Inventors: Ian R. Chester, Littlehampton; Lawson W. Powell, Worthing; David G. Roberts, Storrington, all of England

[73] Assignee: Beecham Group Limited, England

[21] Appl. No.: 312,667

[22] Filed: Oct. 19, 1981

[30] Foreign Application Priority Data

Nov. 5, 1980 [GB] United Kingdom ................. 8035454

[51] Int. Cl.$^3$ ............................................. C12P 37/00
[52] U.S. Cl. ...................................................... 435/43
[58] Field of Search ............................. 435/43, 47, 49

[56] References Cited

U.S. PATENT DOCUMENTS 3,528,965  9/1970  Cole et al. ......................... 435/43 X
3,972,774  8/1976  Brannon ................................. 435/47
4,346,168  8/1982  Cole et al. ............................. 435/43
4,347,314  8/1982  Cole et al. ............................. 435/43

*Primary Examiner*—Lionel M. Shapiro
*Attorney, Agent, or Firm*—Jacobs & Jacobs

[57] ABSTRACT

A process for the preparation of a compound of formula (I):

$$R^2-NH-\underset{O}{\overset{R^1}{\diagup\!\!\!\diagdown}}\underset{N}{\diagup\!\!\!\diagdown}\underset{}{\diagup\!\!\!\diagdown}_{CO_2H}^{S} \quad (I)$$

wherein
$R^1$ is hydrogen, hydroxy, mercapto radical, a substituted or unsubstituted methoxy, ethoxy, methyl, ethyl, methyl thio, or ethylthio radical, a carbamoyloxy, carbamoylthio, $C_{1-6}$ alkanoyloxy, $C_{1-6}$ alkanoylthio, cyano, carboxy or carbamoyl radical; and
$R^2$ represents an acyl group which comprises hydrolysis of a compound of formula (II):

$$R^2-NH-\underset{O}{\overset{R^1}{\diagup\!\!\!\diagdown}}\underset{N}{\diagup\!\!\!\diagdown}\underset{}{\diagup\!\!\!\diagdown}_{CO_2R^3}^{S} \quad (II)$$

wherein $R^1$ and $R^2$ are as defined with respect to formula (I) hereinbefore and $R^3$ represents benzyl or substituted benzyl; wherein the hydrolysis is catalyzed by a microbial serine proteinase.

14 Claims, 3 Drawing Figures

Fig. 2

Fig. 3

PROCESS FOR THE PREPARATION OF PENICILLINS AND PENICILLIN DERIVATIVES

This invention relates to a process for the preparation of penicillins and penicillin derivatives, and in particular to the preparation of penicillins and penicillin derivatives with a 3-carboxylic acid group by the enzymatic hydrolysis of an esterified derivative.

In the course of chemical modification of the penicillin molecule it is frequently necessary to protect the reactive $C_3$ carboxylic acid function as an ester. On completion of the chemical transformation the protecting ester group is removed to regenerate the free carboxyl group. Choice of a suitable protecting group is dictated by the necessity of the group to withstand the chemical reactions carried out on the rest of the molecule and the necessity for the protecting group to be removable without destruction of the remainder of the molecule.

A particularly advantageous protecting group is the benzyl or substituted benzyl ester; this protecting group is readily coupled to the $C_3$ carboxylic acid group of the penicillin nucleus and is stable to many reagents used in the modification of penicillins. Benzyl and substituted benzyl esters may be removed with difficulty by acid or base hydrolysis; however, owing to the destruction of the β-lactam ring under these conditions, the group is more suitably removed by hydrogenolysis in the presence of a noble metal catalyst.

The removal of benzyl and substituted benzyl ester protecting groups using hydrogenolysis has been used extensively on the research scale; whereas, the necessity for special flame-proof equipment, large quantities of very expensive catalysts and rigorous removal of spent catalyst from the resulting pharmacuetical has limited its use in the industrial preparation of pharmaceutical products.

We have now found an enzymatic process for the removal of benzyl and substituted benzyl esters which proceeds in high yield under suitably mild conditions such that destruction of the β-lactam ring is avoided. The process avoids the use of hazardous reagents, such as hydrogen, and expensive reagents, such as a noble metal catalyst.

U.S. Pat. No. 3,972,774 discloses an enzymic process for the removal of a p-nitrobenzyl ester from the $C_4$ carboxyl group of cephalosporins. The process is limited to removal of the p-nitrobenzyl ester using an esterase enzyme produced by a microorganism selected from the group consisting of *Bacillus cereus, Bacillus circulans, Bacillus licheniformis* ATCC 7072 or *Bacillus subtilis*.

The present invention is based on our discovery that most esterase enzymes do not cleave benzyl and substituted benzyl esters of the penicillin 3-carboxyl group.

Accordingly the present invention provides a process for the preparation of a compound of formula (I):

wherein
  $R^1$ is hydrogen, hydroxy, mercapto radical, a substituted or unsubstituted methoxy, ethoxy, methyl, ethyl, methyl thio, or ethylthio radical, a carbamoyloxy, carbamoylthio, $C_{1-6}$ alkanoyloxy, $C_{1-6}$ alkanoylthio, cyano, carboxy or carbamoyl radical; and $R^2$ represents an acyl group which comprises hydrolysis of a compound of formula (II):

wherein $R^1$ and $R^2$ are as defined with respect to formula (I) hereinbefore and $R^3$ represents benzyl or substituted benzyl; characterised in that the hydrolysis is catalysed by a microbial serine proteinase.

Suitably the microbial serine proteinase for use in the present process will be an alkaline microbial serine proteinase, such as subtilisin and, in particular subtilisin A and subtilisin BPN (Enzyme Commission No. EC 3.4.21.14).

The compounds produced by the process of the present invention may be active antibacterial agents or may be useful intermediates in the preparation of active compounds.

Suitable acyl groups $R^2$ include those of the sub-formulae (a)–(d):

$$A_1-(CH_2)_n-\underset{X}{CH}-(CH_2)_m-CO \qquad (a)$$

$$A_2-CO \qquad (b)$$

$$A_2-X_2-(CH_2)_n-CO \qquad (d)$$

wherein n is 0, 1 or 2; m is 0, 1 or 2; $A_1$ is $C_1$–$C_6$ alkyl, $C_3$–$C_6$ cycloalkyl, cyclohexenyl, cyclohexadienyl, phenyl, hydroxy-phenyl, thienyl or pyridyl group; X is a hydrogen or halogen atom, a carboxylic acid, carboxylic ester, azido, tetrazolyl, hydroxy, acyloxy, amino, ureido, guanidino or acylureido group; $A_2$ is an aromatic group such as a phenyl, a 2,6-dimethoxyphenyl, 2-alkoxy-1-naphthyl, 3-arylisoxazolyl or 3-aryl-5-methylisoxazolyl group; $X_1$ is a $CH_2OCH_2$, $CH_2SCH_2$ or $(CH_2)_n$ group; $X_2$ is an oxygen or sulphur atom.

Favoured groups $R^2$ for inclusion in the compounds of the formula (II) include those of the sub-formulae (e) and (f):

wherein $R^6$ is a phenyl, thienyl or phenoxy group; $R^7$ is a hydrogen atom or methyl group; $R^8$ is a phenyl, p-hydroxyphenyl, thienyl or carboxylic acid group; and $R^9$ is a hydroxyl, amino or carboxylic acid group or lower alkyl or phenyl, tolyl or indanyl ester thereof.

One subgroup of compounds within formula (II) which are suitable for deprotection by the process of the present invention are the compounds of formula (III):

wherein $R^3$ is as defined with respect to formula (II) hereinbefore, $R^4$ represents phenyl or 2- or 3-thienyl, and $R^x$ represents hydrogen or an ester-forming radical.

Preferably $R^4$ is 3-thienyl and $R^3$ is benzyl.

Preferably $R^x$ is hydrogen.

Suitable groups $R^3$ in the compounds of formula (II) include benzyl, optionally substituted with $C_{1-6}$ alkyl, $C_{1-6}$ alkoxy, halogen, $C_{1-6}$ alkanoyl, $C_{1-6}$ alkoxycarbonyl, nitro or di($C_{1-6}$) alkylamino.

Preferred groups $R^3$ include benzyl, optionally substituted with $C_{1-6}$ alkyl, $C_{1-6}$ alkoxy, chloro, bromo, fluoro or nitro. For example $R^3$ may advantageously represent benzyl, p-methoxybenzyl, p-chlorobenzyl or p-nitrobenzyl. A particularly preferred group $R^3$ is benzyl.

The microbial serine proteinase may be used in purified form, partially purified form or as obtained in an impure state as a filtrate from a microbial culture medium.

Most suitably the enzyme is at least partially purified to remove other enzymes which might catalyse the destruction of the penicillin or penicillin derivative. The enzyme may be employed itself or attached to an insoluble support either by adsorption, adsorption and cross-linking, for example as disclosed in British Pat. No. 1,264,147, or by covalent bonds either directly or indirectly via bridging groups, for example as described in British Pat. Nos. 1,349,498, 1,387,460 and 1,365,886. Alternatively the enzyme may be bound to a water soluble polymeric support (see British Pat. Nos. 1,284,925 and 1,449,808) so that the enzyme/polymer complexes are recoverable from the aqueous reaction mixture by ultrafiltration; or the enzyme may be attached to non-polar groups (and optionally polymeric supports) as described in British Pat. No. 1,463,513, to render the preparation separable from aqueous media by virtue of the affinity for water-immiscible liquids.

Accordingly in a preferred embodiment of the present invention the microbial serine proteinase is attached to an insoluble support by adsorbtion and crosslinking or covalent bonding.

Suitable insoluble supports to which the enzyme may be attached by adsorption and crosslinking include weakly acidic cation exchange resins such as Amberlite IRC-50, Diaion WK-10(S) and Amberlite CG-50; suitable crosslinking agents include glutaraldehyde, glyoxal and formaldehyde. The use of glutaraldehyde as crosslinking agent is preferred.

Suitable insoluble supports to which the enzyme may be attached by covalent bonding include chemically modified polydextrans such as, for example, cyanogen bromide treated Sepharose, or modified polyacrylamides such as, for example, Enzacryl AH.

Although it is possible to perform the enzymation, reaction by stirring a solution of a compound of formula (II) with the polymeric support in a batchwise process utilising a stirred tank, mechanical damage of the polymeric support may occur.

The process of this invention may preferably be carried out in a column operation rather than a stirred tank process. Thus a column is filled with enzyme supported on a water-insoluble support, such as those described above. This column is then fed at the top with an aqueous solution of the penicillin. The length of the column, the feed rates and the concentrations of the feed solutions may be adjusted so that complete enzymatic hydrolysis occurs and the deprotected penicillin is recovered at the foot of the column. Alternatively the penicillin solution can be recirculated through a shallow column and recirculation continued until the penicillin is substantially converted to the deprotected form. The use of a column process prolongs the life time of the immobilised enzyme because attrition of the solid supports due to agitation, which occurs in a stirred tank process, is eliminated.

The hydrolysis reaction of the present invention is carried out in aqueous media, the reaction mixture being maintained in the range pH 4 to 10.5, preferably pH 6 to 9 especially about pH 7.5 to 8.5. The pH is controlled either by using buffers such as for example borate, phosphate, citrate, tris(hydroxymethyl)aminomethane, and hepes buffer, or by continuous addition of aqueous alkali metal hydroxide, such as sodium hydroxide or potassium hydroxide, ammonia or amines such as triethylamine until reaction is complete.

The preferred buffer system is phosphate buffer at pH 8.5.

The preferred aqueous alkali metal hydroxide for controlling pH is sodium hydroxide. The enzyme substrate is suitably dissolved in buffer before mixing with the enzyme. The concentration of substrate solution will depend upon the solubility of the substrate; suitably the concentration of the substrate solution is in the range of 5% w/v to 2% w/v, preferably 5% w/v.

The temperature of the reaction should be suitable for the enzyme employed and is generally in the range 0° C. to 70° C., more suitably in the range 10° C. to 50° C. and preferably 30° C. to 40° C.

The reaction time depends on such factors as concentrations of reactants, temperature and pH. The choice of temperature for carrying out the enzyme reaction will be a balance between increasing the temperature which will increase the rate of reaction and decreasing the temperature which will in general decrease the rate of decomposition of the enzyme. The enzyme substrate and product, ie compounds of formula (I) and (II) are also generally less stable the higher the pH and the higher the temperature of the reaction medium, and choice of conditions for the reaction will be a balance between increasing pH and/or temperature which will increase the rate of reaction and reduce the length of time the substrate and product will be subjected to the unfavourable conditions or lowering the pH and/or temperature which increase the time that the substrate and product will be held in aqueous media.

After the reaction is complete the reaction mixture is where possible separated from the enzyme and the reaction mixture is acidified and the penicillin derivative of formula (I) isolated by conventional methods.

The amount of enzyme or enzyme containing material required in a given reaction may be assessed by preliminary small-scale trial runs to determine the activity of the enzyme towards the substrate employed.

The invention is illustrated by the following Examples.

The enzymes used in the Examples and Descriptions were obtained from the following sources:
Sigma London Chemical Co Ltd
Fancy Road
Poole
Dorset
C P Laboratories Ltd
PO Box 22
Bishops Stortford
Herts
Novo Enzyme Products Ltd
2B Thames Avenue
Windsor
Berks
ABM Chemicals Ltd
Woodley
Stockport
Cheshire The polymeric supports used in the Examples and Descriptions were obtained from the following sources:
Enzacryl AH and Enzacryl TlO
Koch-Light Laboratories Ltd
Poyle Trading Estate
Colnbrook
Buckinghamshire
Amberlite IRC-50 and CG-50
Lennig Chemicals Ltd
Lennig House
2 Masons Avenue Croydon
Surrey
Diaion WK-10
Mitsubishi Chemical Industries Limited
5-2 Marunouchi 2-chome
Chiyoda-ku, Tokyo
Japan
Sepharose
Pharmacia (Great Britain) Ltd
Paramount House
75 Uxbridge Road
London W5

The activity of the enzyme and enzyme complexes is defined in terms of a unit being the amount of activity required to produce 1 $\mu$g of 6$\beta$-[2-(2-carboxy)-2-thien-3'-ylacetamido 6$\alpha$-methoxy] penicillin in 5 minutes at 37° C. and pH 7.5.

DESCRIPTION 1

Coupling of subtilisin A to CNBr-activated Sepharose 4B

CNBr-activated Sepharose 4B (30 g) was added to hydrochloric acid (0.001 M, 2 dm$^3$) and the mixture was gently stirred for 15 minutes after which the Sepharose was removed by filtration and stirred for 15 minutes in a solution of sodium tetraborate (0.1 M, 1 dm$^3$) containing sodium chloride (0.5 M). After filtration, the Sepharose was again washed with sodium tetraborate/sodium chloride solution for 15 minutes and was then removed by filtration and added to a solution of sodium tetraborate (150 ml, 0.1 M, adjusted to pH 8 with glacial acetic acid) containing subtilisin A (1.9 g, Novo Industri A/S, Copenhagen, Denmark) and stirred for 3 hours at room temperature. The coupled enzyme preparation was filtered off and stirred for 15 minutes in sodium tetraborate (2 dm$^3$, 0.1 M, pH 8) when it was again filtered off and then stirred for 15 minutes in a solution of ethanolamine (3 dm$^3$, 1 M, adjusted to pH 8 with glacial acetic acid) for 2 hours. After filtration the Sepharose was stirred in a solution of sodium tetraborate (2 dm$^3$, 0.1 M) containing sodium chloride (1 M) for 15 minutes and then finally washed extensively with water on a filter. The filtered immobilised enzyme was stored as a damp gel.

Total activity challenged 986,250 units
Enzyme uptake 87.2%
Final weight 100.8 g
Activity 5550 units/g
Overall efficiency 56.8%
Coupling efficiency 65.1%

DESCRIPTION 2

Coupling of Alcalase to CNBr-activated Sepharose 4B

Alcalase 0.6 L was diluted (1:1, v/v) with distilled water and dialysed until the conductivity was 1–2.5 mmho. This enzyme (150 ml) was then stirred for 3 hours at pH 8 with CNBr-activated Sepharose 4B (15 g) which was washed as described in Description 1. The immobilised enzyme was recovered by filtration and treated as in Description 1.

Enzyme challenge 450,000 units
Enzyme uptake 59.7%
Final weight 45.8 g
Activity 4144 units/g
Overall efficiency 42.2%
Coupling efficiency 70.6%

DESCRIPTION 3

Coupling of Alcalase to Enzacryl AH

Enzacryl AH (50 g) was added to hydrochloric acid (1000 ml, 2 M) at 0° C. Sodium nitrite (4%, 400 ml, 0° C.) was added and the mixture stirred for 15 minutes. The Enzacryl was recovered by filtration, washed with sodium phosphate (0.02 M, pH 7.8, 0° C.) and added to a dialysed solution of Alcalase (615 ml, 0° C., 0.02 M in sodium phosphate). The mixture was stirred for 48 hours at 0°–5° C. after which the immobilised enzyme preparation was recovered by filtration and washed with sodium phosphate (0.02 M, pH 7.8).

Enzyme challenge 3,997,500 units
Enzyme uptake 77.1%
Resin weight 117.8 g
Activity 2732 units/g
Overall efficiency 8.1%
Coupling efficiency 10.4%

DESCRIPTION 4

Coupling of Alcalase to Enzacryl TIO

Enzacryl TIO (50 g) was added to a solution of sodium acetate (1000 ml, 0.2 M, pH 5.5) at 0° C. and the mixture was very gently agitated for 5 minutes. The Enzacryl TIO was recovered by filtration and added to a mixture (1:1, v/v) of dialysed Alcalase (307 ml) and sodium acetate (0.4 M, pH 5.5) at 0° C. The mixture was gently stirred for 2 hours after which a saturated solution of 2-naphthol in saturated sodium acetate (500 ml) was added and the stirring continued for a further 2 hours. The immobilised enzyme was recovered by filtration and washed with sodium acetate (0.2 M).

Enzyme challenge 1,995,500 units
Enzyme uptake 89.8%
Resin weight 56.8 g
Activity 1598 units/g
Overall efficiency 4.5%
Coupling efficiency 5.1%

DESCRIPTION 5

Coupling of Alcalase to IRC-50

Dialysed Alcalase 0.6 L (120 ml, prepared as in Description 2) was mixed with IRC-50 (15 g) and stirred overnight the pH being maintained at 6.4 by the addition of sodium hydroxide (1 M). The resin was then filtered off and stirred in a solution of glutaraldehyde (3%, pH 6.4) for 3 hours after which the enzyme-resin was recovered by filtration and washed extensively with distilled water. The preparation was stirred in sodium phosphate (0.02 M, pH 7.8) and the mixture equilibrated to pH 7.5 overnight by the addition of sodium hydroxide (1 M). The enzyme-resin was then washed with distilled water.

Enzyme challenge 315,770 units
Enzyme uptake 84.8%
final weight 22.9 g
Final activity 2210 units/g
Overall efficiency 16.0%
Coupling efficiency 18.9%

DESCRIPTION 6

Coupling of Alcalase to WK-10(S)

Dialysed Alcalase 0.6 L (300 ml, prepared as in Description 2) was mixed with WK-10(S) (50 g) and stirred for 4 hours with the pH maintained at 6.0 by the addition of sodium hydroxide (1 M). The resin was then recovered by filtration and cross-linked, equilibrated and washed as in Description 5.

Enzyme challenge 1,500,000 units
Enzyme uptake 89.6%
Resin weight 56.5 g
Activity 7202 units/g
Overall efficiency 27.1%
Coupling efficiency 30.2%

DESCRIPTION 7

Coupling of Alcalase to CG-50

Dialysed Alcalase 0.6 L (400 ml, prepared as in Description 2) was mixed with CG-50 (50 g) and stirred overnight with the pH maintained at 5.8 by the addition of sodium hydroxide (1 M). Subsequently, the CG-50 was recovered by filtration and cross-linked, equilibrated and washed as in Description 5.

Enzyme challenge 2,000,000 units
Enzyme uptake 52.9%
Weight 55.5 g
Activity 6160 units/g
Overall efficiency 17.1%
Coupling efficiency 32.3%

DESCRIPTION 8

Coupling of Subtilisin A to CG-50

Subtilisin A (3 g) was dissolved in distilled water (150 ml) and CG-50 (50 g) was added to the stirred mixture. The pH was maintained at 5.8 overnight after which the CG-50 was recovered by filtration, cross-linked, equilibrated and washed as in Description 5.

Enzyme challenge 2,000,000 units
Enzyme uptake 90.9%
Final weight 53.5 g
Activity 6811 units/g
Overall efficiency 18.2%
Coupling efficiency 20.0%

EXAMPLE 1

De-esterification of benzyl 6β-[2-(2-carboxy)-2-thien-3'-ylacetamido]-6α-methoxy]penicillanate In order to determine the amount of hydrolysis of the benzyl ester of the $C_3$ carboxyl group by a number of enzymes, the ester was subjected, in aqueous reaction mixture, to the action of the particular enzyme using the following procedure and assay procedure.

Ester solution—Ester (50 mg) was added slowly to stirred 0.25 M, pH 7.8 phosphate buffer (1 ml). When the ester was dissolved distilled water (9 ml) was added.

Enzyme solution—Enzyme (5 mg) was dissolved in distilled water (1 ml).

Enzymation—Enzyme solution (0.2 ml) was added to ester solution (2 ml) and the mixture was incubated at 37° C. for 16 hours.

Assay—When the incubation was complete, the reaction mixture was filtered through glass fibre (Whatman GF/A) and assayed for disappearance of the ester by HPLC.

ASSAY SYSTEMS (HPLC) FOR EXAMPLES 1 AND 2

| | For determination of the ester concentration |
|---|---|
| (1) | Column Brownlee $C_8$ (MPLC) |
| | Buffer:- 45% acetonitrile |
| | 0.05 M sodium propionate |
| | pH 4.7 (adjusted with glacial acetic acid) |
| | Flow rate 1 ml/min |
| | Detector wavelength 254 nm |
| | For determination of the acid concentration |
| (2) | Column Water $C_{18}$ Bondapak |
| | Buffer:- 10% methanol |
| | 0.05 M ammonium acetate |
| | Flow rate 1.5 ml/min |
| | Detector wavelength 220 nm |

Extent of conversion of ester to acid is determined as follows:

$$\frac{\text{Initial concentration of ester } - \text{ Final concentration of Ester } (HPLC)}{\text{Initial concentration of Ester } (HPCL)} \times 100\% = \text{Extent of conversion}$$

In table 1 the extent of conversion of ester to acid is shown for a number of samples of the enzyme of the present invention.

TABLE 1

| Experiment | Enzyme | Supplier | Conversion |
|---|---|---|---|
| 1 | Alcalase 1.5 M (Subtilisin A) B licheniformis | Novo | 88.6% |
| 2 | Alcalase 0.6 L (Subtilisin A) B licheniformis | Novo | 30.0% |
| 3 | Protease type VII B amyloliquefaciens, Nagarase; Subtilisin BPN | Sigma | 70.0% |
| 4 | Protease type VIII B subtilis, Subtilisin Carlsberg; Subtilopeptidase A | Sigma | 89.0% |
| 5 | Protease type XI Tritirachium album Proteinase K | Sigma | 61.0% |
| 6 | Protease Bacterial (Subtilisin A) B Sublitisin | CP | 91.5% |
| 7 | Proteinase D (Subtilisin A) B licheniformis | ABM | 100.0% |

TABLE 1-continued

| Experiment | Enzyme | Supplier | Conversion* |
|---|---|---|---|
| 8 | Subtilisin A, B licheniformis | Novo | 88.8% |

*Percentage conversion of the ester to 6β-[2-(2-carboxy)-2-thien-3'-ylacetamido 6α-methoxy] penicillin.

EXAMPLE 2

De-esterification of benzyl 6β-[2-(2-carboxy)-2-thien-3'-ylacetamido 6α-methoxy]penicillanate using subtilisin A Benzyl 6β-[2-(2-carboxy)-2-thien-3'-ylacetamido 6α-methoxy]penicillanate (0.825 g) was dissolved by adding slowly to stirred 0.25 M, pH 7.8 phosphate buffer (8 ml).

Subtilisin A (28.16 mg) was dissolved in distilled water (10 ml).

Ester solution (3 ml) was added to distilled water (7 ml) and heated to 37° C. in a stirred, water jacketed glass vessel (60 ml) and the pH adjusted to 7.5 by the addition of 1 M NaOH. Subtilisin A solution (10 ml) was heated to 37° C. and added to the ester. The mixture was stirred, the temperature maintained at 37° C. and the pH maintained at 7.5 by the addition of 0.1 M sodium hydroxide.

Samples were removed at appropriate intervals and assayed for ester and acid using the two HPLC systems described in Example 1.

The conversion of ester to acid after 4 hours reaction was determined by the above procedure to be 88%.

EXAMPLE 3

Figure 1:
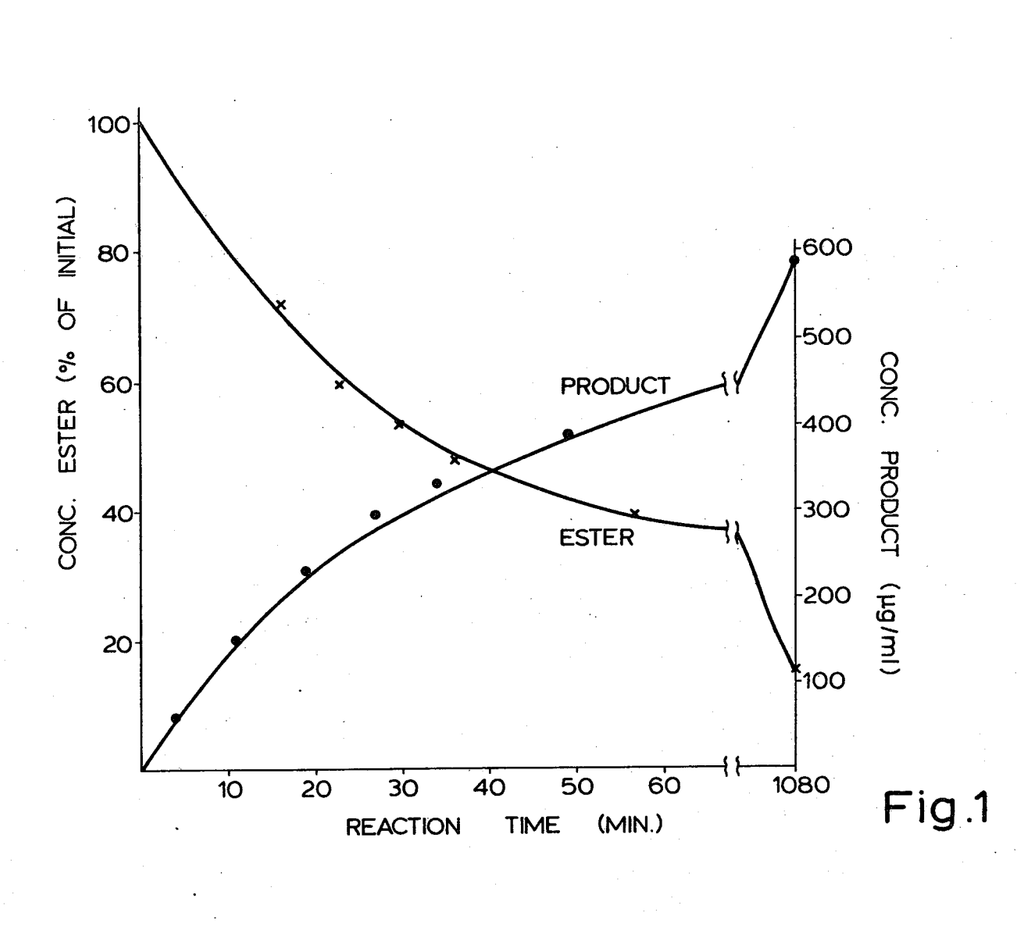

Conversion of benzyl 6β-[2-(2-carboxy)-2-thien-3'-ylacetamido 6α-methoxy]penicillanate to 6β-[2-(2-carboxy)-2-thien-3'-ylacetamido 6α-methoxy]penicillin using Subtilisin A Benzyl 6β-[2-(2-carboxy)-2-thien-3'-ylacetamido]-penicillanate was dissolved (1069 μg/ml) in sodium phosphate (25 ml, 0.05 M, pH 7.8). Subtilisin A (10.3 mg) was added and the solution allowed to stand at room temperature for 18 hours. Benzyl 6β-[2-(2-carboxy)-2-thien-3'-ylacetamido 6α-methoxy]penicillanate and 6β-[2-(2-carboxy)-2-thien-3'-ylacetamido 6α-methoxy]-penicillin levels were monitored by HPLC and are shown in FIG. 1.

EXAMPLE 4

Figure 2:
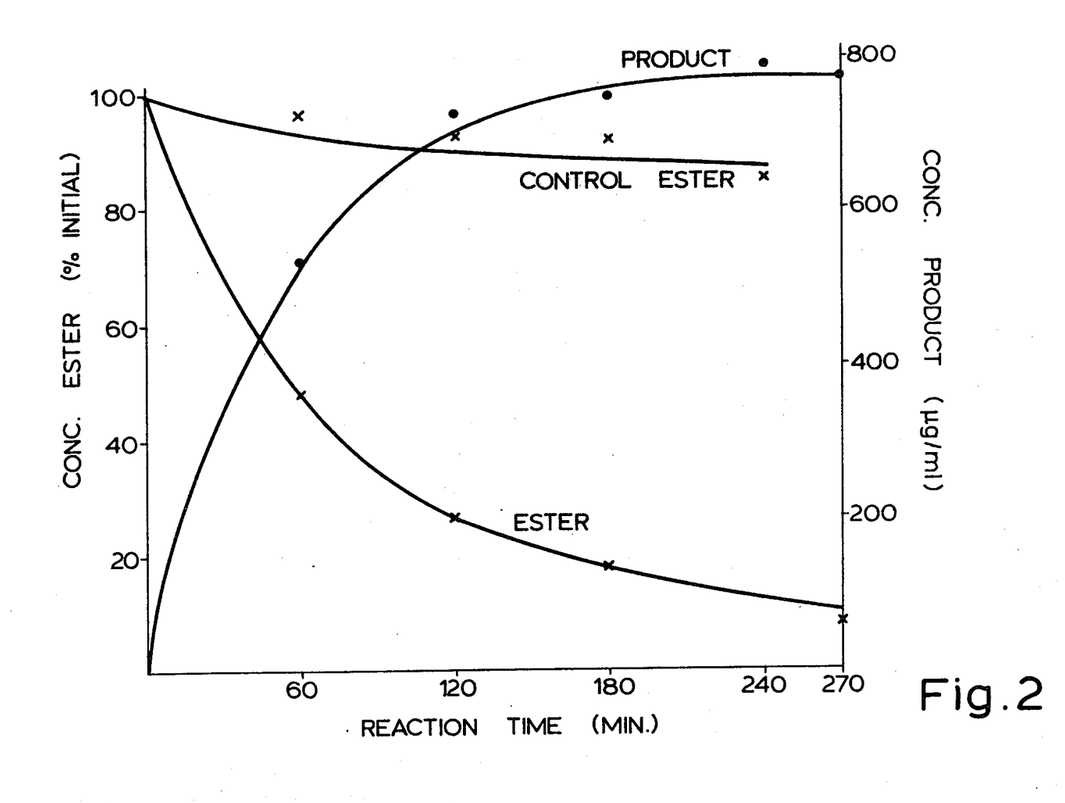

Conversion of benzyl 6β-[2-(2-carboxy)-2-thien-3'-ylacetamido 6α-methoxy]penicillanate to 6β-[2-(2-carboxy)-2-thien-3'-ylacetamido 6α-methoxy]penicillin using Subtilisin A Benzyl 6β-[2-(2-carboxy)-2-thien-3'-ylacetamido]-penicillanate (0.8 g) was dissolved in sodium phosphate (8 ml, 0.2 M, pH 7.8) and an aliquot (3 ml) was mixed with distilled water (7 ml). The mixture was heated to 37° C. and the pH adjusted to 7.5 with sodium hydroxide (0.1 M) after which a solution of subtilisin A (10 ml containing 28.16 mg), which had been pre-heated to 37° C., was added. The temperature was maintained at 37° C. and the pH was maintained at 7.5 by the addition of sodium hydroxide (0.1 M). The disappearance of the benzyl 6β-[2-(2-carboxy)-2-thien-3'-ylacetamido 6α-methoxy]penicillanate and the appearance of the 6β-[2-(2-carboxy)-2-thien-3'-ylacetamido 6α-methoxy]penicillin was monitored by HPLC as shown in FIG. 2.

A control experiment which contained no subtilisin was carried out and the disappearance of the 6β-[2-(2-carboxy)-2-thien-3'-ylacetamido 6α-methoxy]penicillanate monitored.

EXAMPLE 5

Conversion of benzyl 6β-[2-(2-carboxy)-2-thien-3'-ylacetamido 6α-methoxy]penicillanate to 6β-[2-(2-carboxy)-2-thien-3'-ylacetamido 6α-methoxy]penicillin using the immobilised (CG-50) preparation of Alcalase of Description 7

Figure 3:
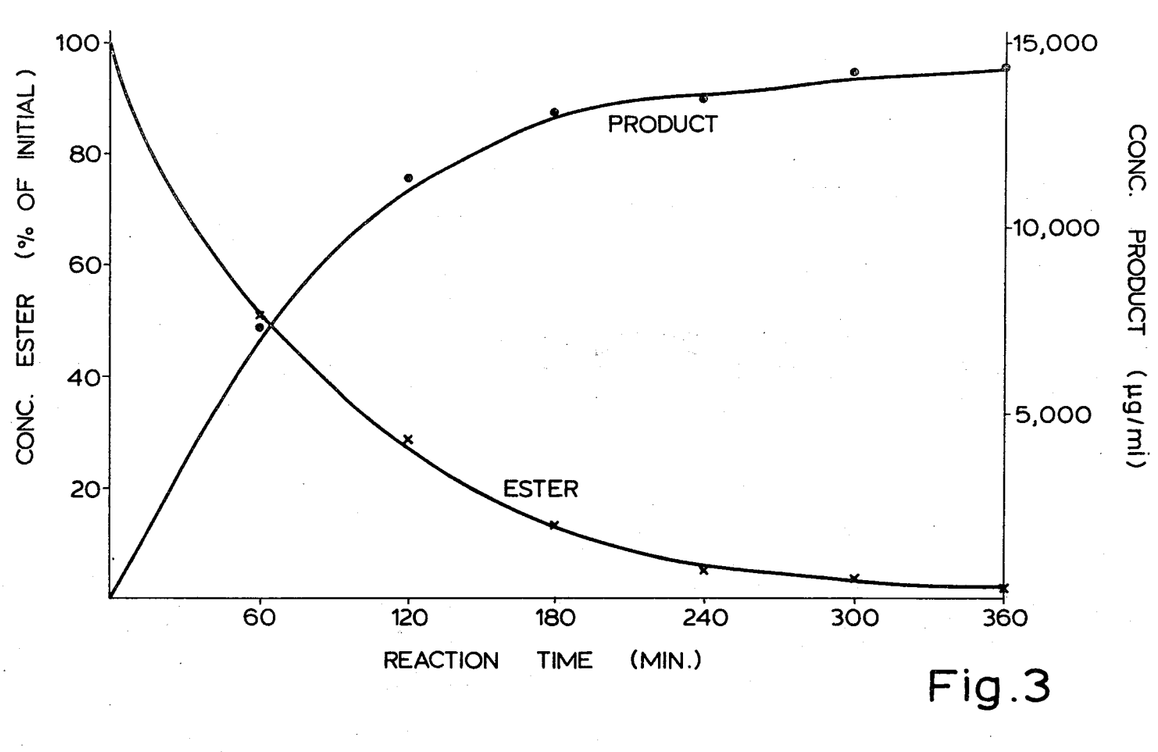

Benzyl 6β-[2-(2-carboxy)-2-thien-3'-ylacetamido]-penicillanate (6 g) was dissolved in sodium phosphate (35 ml, 0.25 M, pH 7.8) and the pH adjusted to 7.5 by the addition of sodium hydroxide (5 M) before a final adjustment of the volume to 50.5 ml. An aliquot (25 ml) of the ester was added to a stirred mixture of the CG-50-Alcalase preparation (60 g) and distilled water which was maintained at 37° C. A further aliquot of ester (25 ml) was added to the mixture as a linear feed over 2 hours. The reaction mixture was maintained at 37° C. and the pH was adjusted to 8 by the addition of sodium hydroxide. The disappearance of the substrate and appearance of the product was determined by HPLC as shown in FIG. 3.

Over a series of four enzymations the average yield was 91.8% and the activity retained was 76% of the initial.

Benzyl 6β-[2-(2-carboxy)-2-thien-3'-ylacetamido]-penicillanate is similarly converted to 6β-[2-(2-carboxy)-2-thien-3'-ylacetamido 6α-methoxy]penicillin using the supported enzymes prepared in Descriptions 1 to 6 and 8.

ASSAY SYSTEMS (HPCL) FOR EXAMPLES 3, 4 AND 5

| For determination of the ester concentration | |
|---|---|
| Column | Waters $C_{18}$ Bondapak |
| Buffer:- | 35% acetonitrile |
| | 0.04 M sodium propionate |
| | pH unadjusted |
| | Flow rate 2 ml/min |
| Detector wavelength 20 nm | |
| For determination of the acid concentration | |
| Column | Chromopak RP18 |
| Buffer:- | 6.25% methanol |
| | 0.03 M ammonium acetate |
| | Flow rate 2 ml/min |
| Detector wavelength 240 nm | |

EXAMPLE 6

Column based enzymations of benzyl 6β-[2-(2-carboxy)-2-thien-3'ylacetamido 6α-methoxy]penicillanate A double walled glass column was packed with immobilised enzyme of Description 7 (circa 75 g) and washed overnight with phosphate buffer (0.2 M, pH 8.5) eluting at 20 ml per hour. The column during this period was maintained at 37° C. with preheated water (Churchill circulator).

A solution of benzyl 6β-[2-(2-carboxy)-2-thien-3'-ylacetamido 6α-methoxy]penicillanate (2–5% w/v) in phosphate buffer (0.2 M, pH 8.5) was then pumped onto the column and allowed to elute at such a rate as to render the residual benzyl 6β-[2-(2-carboxy)-2-thien-3-ylacetamido 6α-methoxy]penicillanate concentration less than 3%, (but preferably less than 1%) of the feed concentration.

The 6β-[2-(2-carboxy)-2-thien-3'-ylacetamido 6α-methoxy]penicillin was then extracted from the aqueous eluate with methylisobutyl ketone at pH 2 (2 N HCl). The bulked methylisobutyl ketone solutions were then extracted with aqueous sodium bicarbonate at pH 5.8–6. Residual methylisobutyl ketone was removed from the combined bicarbonate extracts in vacuo, the solution filtered through a millipore filter (0.45μ) and then freeze-dried to give yields of 1.4 to 1.5 g per 100 ml of 2% feed.

ASSAY SYSTEMS (HPLC) FOR EXAMPLE 6

|     | For determination of the ester concentration | |
| --- | --- | --- |
| (1) | Column | Zorbax CN |
|     | Buffer:- | 38% acetonitrile |
|     |          | 0.05 M sodium formate |
|     |          | pH 3.5 (adjusted with 2N NaOH) |
|     |          | Flow rate 1.5 ml/min |
|     | Detector wavelength 254 nm | |
| (2) | Column | Waters $C_{18}$ Bondapak |
|     | Buffer:- | 25% acetonitrile |
|     |          | 0.04 M sodium proprionate |
|     |          | pH 7.5 (adjusted with proprionic acid |
|     |          | Flow rate 2 ml/min |
|     | Detector wavelength 254 nm | |
|     | For determination of the acid concentration | |
| (1) | Column | Waters $C_{18}$ Bondapak |
|     | Buffer:- | 10% methanol |
|     |          | 0.1 M sodium dihydrogen phosphate |
|     |          | pH 7 (adjusted with 2N NaOH) |
|     |          | Flow rate 2 ml/min |
|     | Detector wavelength 254 nm | |

We claim:

1. A process for the preparation of a compound of formula (I):

wherein $R^1$ is hydrogen, hydroxy, mercapto radical, a substituted or unsubstituted methoxy, ethoxy, methyl, ethyl, methyl thio, or ethylthio radical, a carbamoyloxy, carbamoylthio, $C_{1-6}$ alkanoyloxy, $C_{1-6}$ alkanoylthio, cyano, carboxy or carbamoyl radical; and $R^2$ represents an acyl group which comprises hydrolysis of a compound of formula (II):

wherein $R^1$ and $R^2$ are as defined with respect to formula (I) hereinbefore and $R^3$ represents benzyl or substituted benzyl; characterised in that the hydrolysis is catalysed by a microbial serine proteinase.

2. A process as claimed in claim 1 wherein the hydrolysis is catalysed by an alkaline microbial serine proteinase.

3. A process as claimed in claim 1 wherein the hydrolysis is catalysed by subtilisin.

4. A process as claimed in claim 1 wherein the hydrolysis is catalysed by subtilisin A or subtilisin BPN.

5. A process as claimed in claim 1 wherein $R^2$ is of the sub-formulae (a)–(d):

wherein n is 0, 1 or 2; m is 0, 1 or 2; $A_1$ is $C_1$–$C_6$ alkyl, $C_3$–$C_6$ cycloalkyl, cyclohexenyl, cyclohexadienyl, phenyl, hydroxy-phenyl, thienyl or pyridyl group; X is a hydrogen or halogen atom, a carboxylic acid, carboxylic ester, azido, tetrazolyl, hydroxy, acyloxy, amino, ureido, guanidino or acylureido group; $A_2$ is an aromatic group such as a phenyl, a 2,6-dimethoxyphenyl, 2-alkoxy-1-naphthyl, 3-arylisoxazolyl or 3-aryl-5-methylisoxazolyl group; $X_1$ is a $CH_2OCH_2$, $CH_2SCH_2$ or $(CH_2)_n$ group; $X_2$ is an oxygen or sulphur atom.

6. A process as claimed in claim 1 wherein $R^2$ is of the sub-formula (e) or (f):

wherein $R^6$ is a phenyl, thienyl or phenoxy group; $R^7$ is a hydrogen atom or methyl group; $R^8$ is a phenyl, p-hydroxyphenyl, thienyl or carboxylic acid group; and $R^9$ is a hydroxyl, amino or carboxylic acid group or lower alkyl or phenyl, tolyl or indanyl ester thereof.

7. A process as claimed in claim 1 wherein the enzyme hydrolysis is carried out on a compound of formula (III):

wherein $R^3$ is as defined with respect to formula (II) hereinbefore, $R^4$ represents phenyl or 2- or 3-thienyl, and $R^x$ represents hydrogen or an ester-forming radical.

8. A process as claimed in claim 7 wherein $R^4$ is 3-thienyl and $R^3$ is benzyl.

9. A process as claimed in claim 7 wherein $R^x$ is hydrogen.

10. A process as claimed in claim 7 wherein $R^3$ is benzyl, optionally substituted with $C_{1-6}$ alkyl, $C_{1-6}$ alkoxy, halogen, $C_{1-6}$ alkanoyl, $C_{1-6}$ alkoxycarbonyl, nitro or di($C_{1-6}$) alkylamino.

11. A process as claimed in claim 7 wherein $R^3$ is benzyl, optionally substituted with $C_{1-6}$ alkyl, $C_{1-6}$ alkoxy, chloro, bromo, fluoro or nitro.

12. A process as claimed in claim 11 wherein $R^3$ is benzyl.

13. A process as claimed in claim 2 wherein the alkaline microbial serine proteinase is attached to an insoluble support, a water soluble polymeric support, or to non-polar groups to render the preparation separable from aqueous media by virtue of the affinity for water-immiscible liquids.

14. A process as claimed in claim 13 wherein the alkaline microbial serine proteinase is attached to an insoluble support by adsorbtion and crosslinking or covalent bonding.

* * * * *